United States Patent
Liu et al.

(10) Patent No.: US 7,627,392 B2
(45) Date of Patent: Dec. 1, 2009

(54) AUTOMATED PROCESS CONTROL USING PARAMETERS DETERMINED WITH APPROXIMATION AND FINE DIFFRACTION MODELS

(75) Inventors: Wei Liu, Santa Clara, CA (US); Shifang Li, Pleasanton, CA (US); Weidung Yang, Milpitas, CA (US); Manuel Madriaga, San Jose, CA (US)

(73) Assignee: Tokyo Electron Limited, Tokyo (JP)

( * ) Notice: Subject to any disclaimer, the term of this patent is extended or adjusted under 35 U.S.C. 154(b) by 315 days.

(21) Appl. No.: 11/848,214

(22) Filed: Aug. 30, 2007

(65) Prior Publication Data

US 2009/0063077 A1  Mar. 5, 2009

(51) Int. Cl.
*G06F 19/00* (2006.01)

(52) U.S. Cl. .......................... 700/105; 700/29; 700/47; 356/369

(58) Field of Classification Search .................... 700/28, 700/29, 31, 47, 105, 108, 109, 119–121; 702/81, 82, 84, 127, 159, 182; 356/328, 356/369, 625; 703/6, 13
See application file for complete search history.

(56) References Cited

U.S. PATENT DOCUMENTS

| 6,772,084 | B2 * | 8/2004 | Bischoff et al. ............. 702/127 |
| 6,792,328 | B2 * | 9/2004 | Laughery et al. ............ 700/121 |
| 6,891,626 | B2 | 5/2005 | Niu et al. |
| 6,943,900 | B2 | 9/2005 | Jakatdar et al. |
| 7,064,829 | B2 * | 6/2006 | Li et al. ....................... 356/369 |
| 7,065,423 | B2 * | 6/2006 | Prager et al. ................. 700/108 |
| 7,072,049 | B2 * | 7/2006 | Niu et al. ..................... 356/625 |
| 7,379,183 | B2 * | 5/2008 | Mieher et al. ............... 356/369 |
| 2004/0017574 | A1 | 1/2004 | Vuong et al. |
| 2004/0267397 | A1 | 12/2004 | Doddi et al. |
| 2006/0290947 | A1 | 12/2006 | Li et al. |
| 2007/0135959 | A1 | 6/2007 | Vuong et al. |
| 2007/0211260 | A1 * | 9/2007 | Vuong et al. ................. 356/625 |

OTHER PUBLICATIONS

U.S. Appl. No. 11/846,462, filed Aug. 28, 2007 for Liu, et al.
U.S. Appl. No. 11/848,154, filed Aug. 30, 2007 for Liu, et al.

* cited by examiner

*Primary Examiner*—Charles R Kasenge
(74) *Attorney, Agent, or Firm*—Manuel B. Madriaga

(57) ABSTRACT

Provided is a method of controlling a fabrication cluster using a machine learning system, the machine learning system trained developed using an optical metrology model. A simulated approximation diffraction signal is generated based on an approximation diffraction model of the structure. A set of difference diffraction signal is obtained by subtracting the simulated approximation diffraction signal from each of simulated fine diffraction signals and paired with the corresponding profile parameters. A first machine learning system is trained using the pairs of difference diffraction signal and corresponding profile parameters. A library of simulated fine diffraction signals and profile parameters is generated using the trained first machine learning system and using ranges and corresponding resolutions of the profile parameters. A measured diffraction signal is input into the trained second machine learning system to determine at least one profile parameter. The at least one profile parameter is used to adjust at least one process parameter or equipment setting of the fabrication cluster.

20 Claims, 14 Drawing Sheets

AUTOMATED PROCESS CONTROL USING PARAMETERS DETERMINED WITH APPROXIMATION AND FINE DIFFRACTION MODELS

BACKGROUND

1. Field

The present application generally relates to optical metrology of a structure formed on a semiconductor wafer, and, more particularly, to determining one or more profile parameters of a structure using approximation and fine models in optical metrology for use in automated process control.

2. Related Art

In semiconductor manufacturing, periodic gratings are typically used for quality assurance. For example, one typical use of periodic gratings includes fabricating a periodic grating in proximity to the operating structure of a semiconductor chip. The periodic grating is then illuminated with electromagnetic radiation. The electromagnetic radiation that deflects off of the periodic grating is collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured diffraction signal) is compared to a library of simulated diffraction signals. Each simulated diffraction signal in the library is associated with a hypothetical profile. When a match is made between the measured diffraction signal and one of the simulated diffraction signals in the library, the hypothetical profile associated with the simulated diffraction signal is presumed to represent the actual profile of the periodic grating.

Hypothetical profiles, which are used to generate simulated diffraction signals, are generated based on a profile model that characterizes the structure to be examined. Thus, in order to accurately determine the profile of the structure using optical metrology, a profile model that accurately characterizes the structure should be used.

SUMMARY

Provided is a method of controlling a fabrication cluster using a library and/or a machine learning system, the library developed and the machine learning system trained using an optical metrology model, the optical metrology model comprising a profile model, an approximation diffraction model, and a fine diffraction model. A simulated approximation diffraction signal is generated based on an approximation diffraction model of the structure. A set of difference diffraction signals is obtained by subtracting the simulated approximation diffraction signals from each of simulated fine diffraction signals and paired with the corresponding profile parameters. A first machine learning system is trained using the pairs of difference diffraction signals and corresponding profile parameters. A library of simulated fine diffraction signals and profile parameters is generated using the trained first machine learning system and using ranges and corresponding resolutions of the profile parameters. The library is used to train a second machine learning system. A measured diffraction signal is input into the trained second machine learning system to determine at least one profile parameter. The at least one profile parameter is used to adjust at least one process parameter or equipment setting of the fabrication cluster.

DETAILED DESCRIPTION OF EXEMPLARY EMBODIMENT(S)

In order to facilitate the description of the present invention, a semiconductor wafer may be utilized to illustrate an application of the concept. The methods and processes equally apply to other work pieces that have repeating structures. Furthermore, in this application, the term structure when it is not qualified refers to a patterned structure.

Figure 1A:
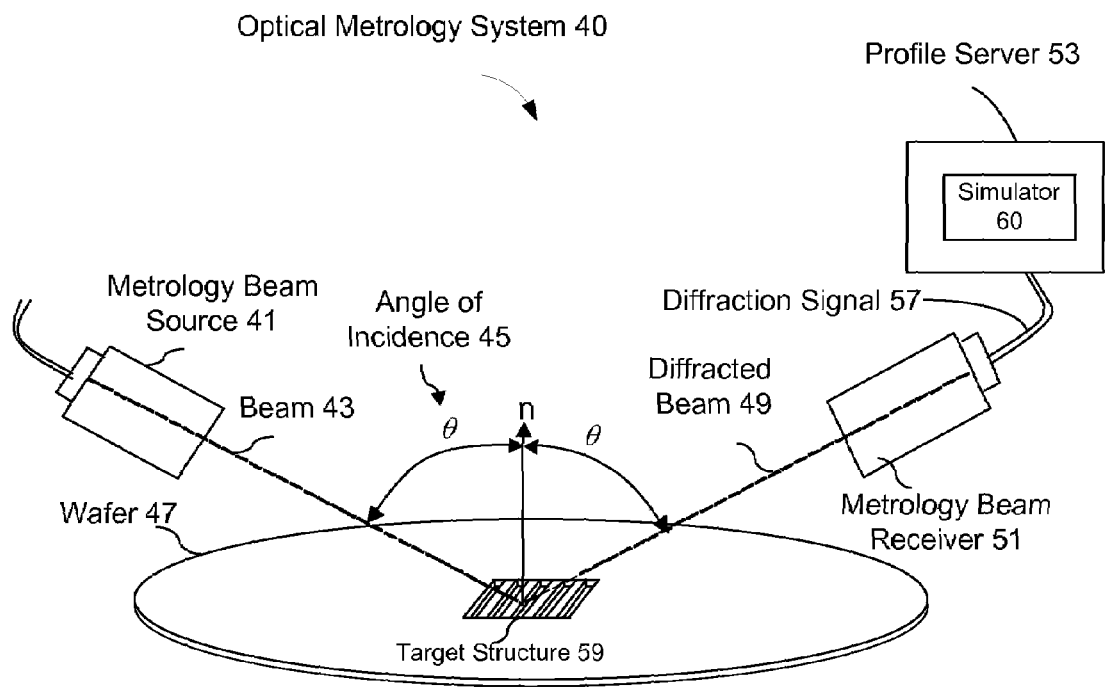
FIG. 1A is an architectural diagram illustrating an exemplary embodiment where optical metrology can be utilized to determine the profiles of structures formed on a semiconductor wafer.

FIG. 1A is an architectural diagram illustrating an exemplary embodiment where optical metrology can be utilized to determine the profiles or shapes of structures fabricated on a semiconductor wafer. The optical metrology system 40 includes a metrology beam source 41 projecting a metrology beam 43 at the target structure 59 of a wafer 47. The metrology beam 43 is projected at an incidence angle θ towards the target structure 59. The diffracted beam 49 is measured by a metrology beam receiver 51. The measured diffraction signal 57 is transmitted to a profile server 53. The profile server 53 compares the measured diffraction signal 57 against simulated diffraction signals and their associated hypothetical profiles representing various combinations of dimensions of the target structure, simulated by and/or stored in simulator 60. The simulator 60 can be either a library that consists of a machine learning system, a pre-generated simulated diffraction signal database, or similar system (e.g. this is library method). Alternatively, it can be an on-demand diffraction signal generator that solves Maxwell's equations for a given profile (e.g. this is the regression method). In an exemplary embodiment, a diffraction signal generated by simulator 60 that best matches the measured diffraction signal 57, is selected. The hypothetical profile and associated dimensions corresponding to the selected simulated diffraction signal are assumed to correspond to the actual profile and dimensions of the features of target structure 59. The optical metrology system 40 may utilize a reflectometer, scatterometer, ellipsometer, or other optical metrology device to measure the diffraction beam or signal. An optical metrology system is described in U.S. Pat. No. 6,943,900, entitled GENERATION OF A LIBRARY OF PERIODIC GRATING DIFFRACTION SIGNAL, issued on Sep. 13, 2005, which is incorporated herein by reference in its entirety.

Simulated diffraction signals can be generated by solving Maxwell's equations using some numerical analysis technique. Various numerical analysis techniques, including variations of rigorous coupled wave analysis (RCWA) can be used. For a more detailed description of RCWA, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety.

Simulated diffraction signals can also be generated using a machine learning system (MLS). Prior to generating the simulated diffraction signals, the MLS is trained using known input and output data. In one exemplary embodiment, simulated diffraction signals can be generated using an MLS employing a machine learning algorithm, such as back-propagation, radial basis function, support vector machine, kernel regression, and the like. For a more detailed description of machine learning systems and algorithms as applied to optical metrology, see U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

Figure 1B:
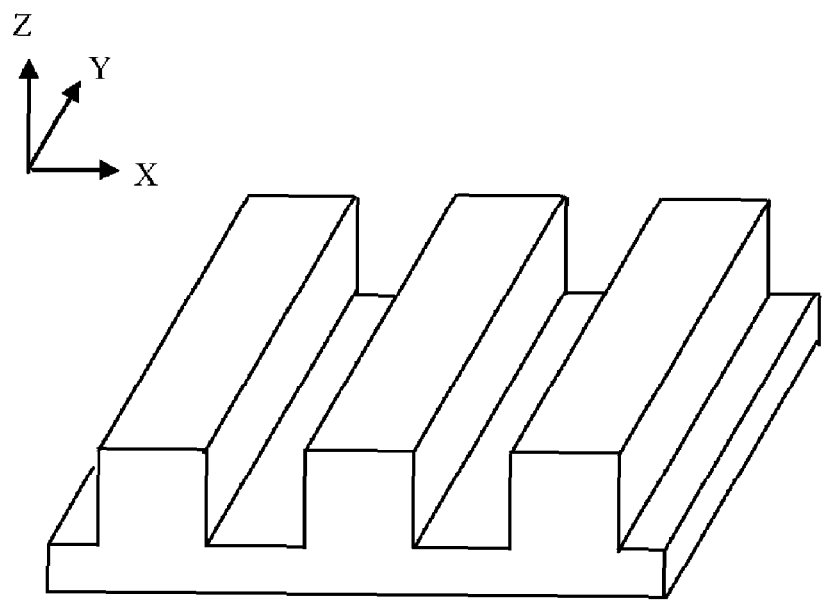
FIG. 1B depicts an exemplary one-dimensional repeating structure.

The term "one-dimensional structure" is used herein to refer to a structure having a profile that varies in one dimension. For example, FIG. 1B depicts a periodic grating having a profile that varies in one dimension (i.e., the x-direction). The profile of the periodic grating depicted in FIG. 1B is assumed to be substantially uniform or continuous in the y-direction.

Figure 1C:
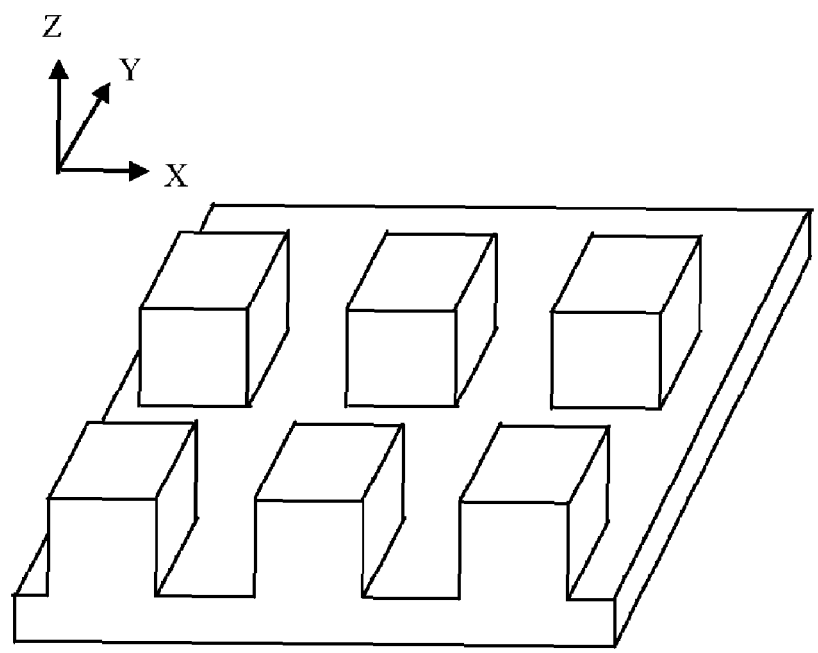
FIG. 1C depicts an exemplary two-dimensional repeating structure

The term "two-dimensional structure" is used herein to refer to a structure having a profile that varies in two-dimensions. For example, FIG. 1C depicts a periodic grating having a profile that varies in two dimensions (i.e., the x-direction and the y-direction).

Figure 2A:
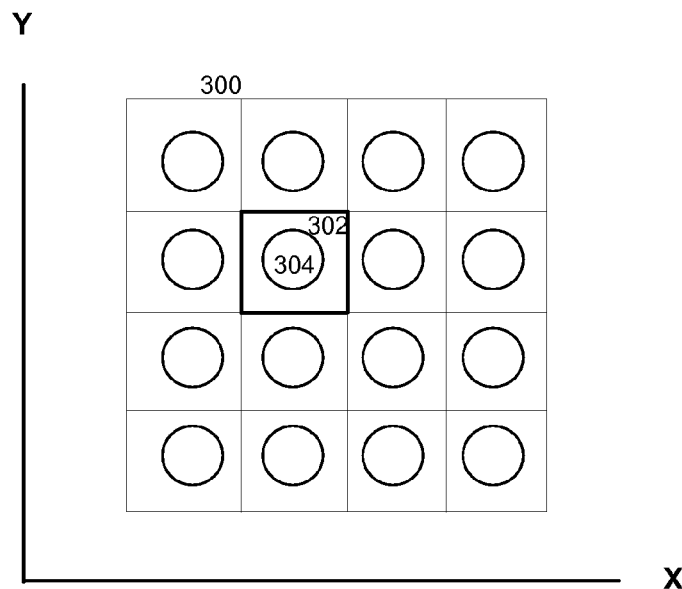
FIG. 2A depicts an exemplary orthogonal grid of unit cells of a two-dimensional repeating structure.
Figure 2B:
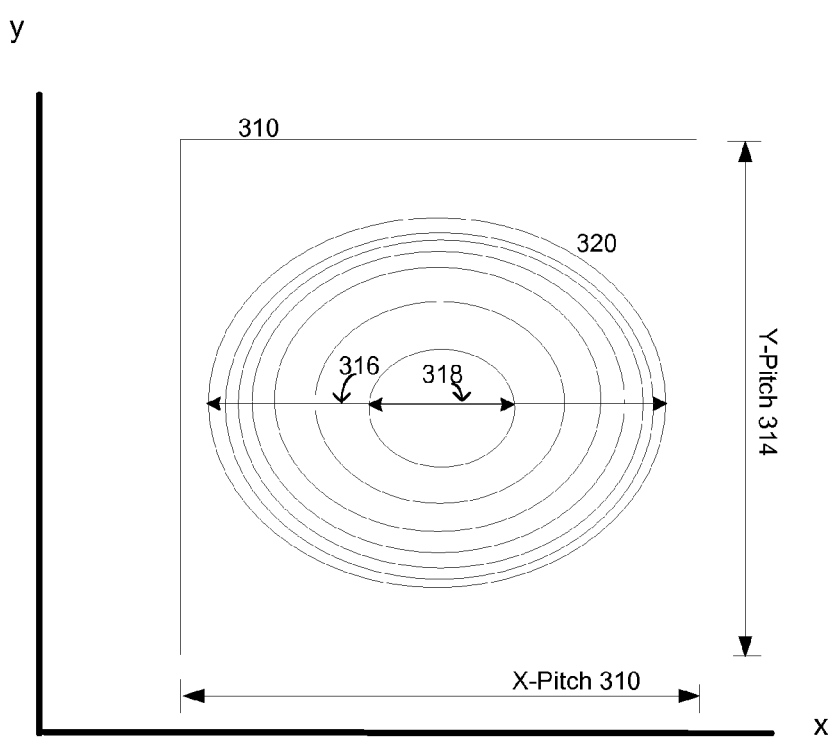
FIG. 2B depicts a top-view of a two-dimensional repeating structure.
Figure 2C:
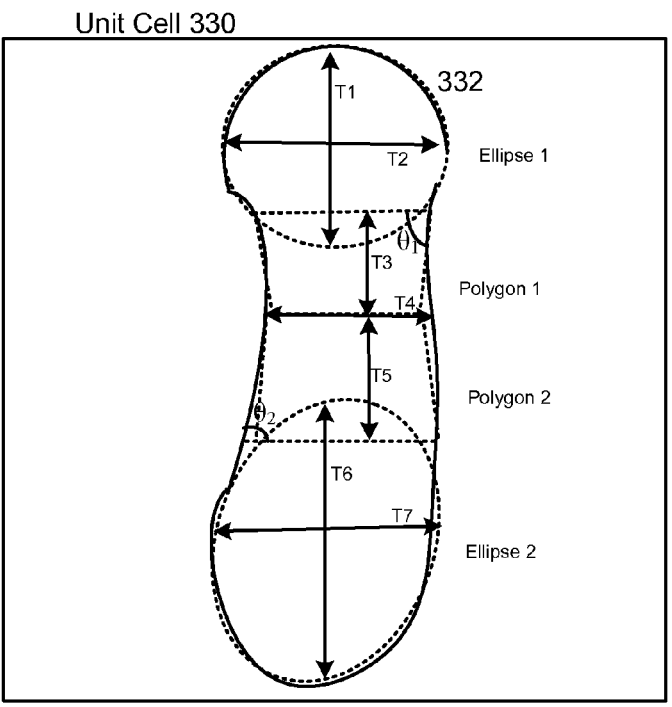
FIG. 2C is an exemplary technique for characterizing the top-view of a two-dimensional repeating structure.

FIGS. 2A, 2B, and 2C describe the characterization of two-dimensional repeating structures for optical metrology modeling. FIG. 2A depicts a top-view of an exemplary orthogonal grid of unit cells of a two-dimensional repeating structure 300. A hypothetical grid of lines is superimposed on the top-view of the repeating structure where the lines of the grid are drawn along the directions of periodicity. The hypothetical grid of lines forms areas referred to as unit cells 302. The unit cells may be arranged in an orthogonal or non-orthogonal configuration. Two-dimensional repeating structures may comprise features such as repeating posts, contact holes, vias, islands, or combinations of two or more shapes within a unit cell. Furthermore, the features may have a variety of shapes and may be concave or convex features or a combination of concave and convex features. Referring to FIG. 2A, the repeating structure 300 comprises unit cells 302 with holes 304 arranged in an orthogonal manner, wherein holes 304 are located substantially at the centers of unit cells 302.

FIG. 2B depicts a top-view of a two-dimensional repeating structure unit cell 310, which includes a concave elliptical hole 320. The dimensions of hole 320 become progressively smaller until the bottom of the hole. Profile parameters used to characterize the structure include the X-pitch 310 and the Y-pitch 314. In addition, the major axis of the ellipse 316 at the top of the hole 320 and the major axis of the ellipse 318 at the bottom of hole 320 may be used to characterize the hole 320. Furthermore, any intermediate major axis between the top and bottom of the hole may also be used as well, as also any minor axis (not shown).

FIG. 2C shows an exemplary technique for characterizing the top-view of a two-dimensional repeating structure. Unit cell 330 includes a feature 332, which is an island with a peanut shape viewed from the top. One modeling approach includes approximating the feature 332 with a combination of ellipses and polygons. Assuming further that after analyzing the production variability of the top-view shape of the feature 332, it has been determined that two ellipses, ellipse 1 and ellipse 2, and two polygons, polygon 1 and polygon 2, may be used to fully characterize feature 332. In turn, parameters needed to characterize the two ellipses and two polygons comprise nine parameters as follows: major and minor axes T1 and T2 for ellipse 1; dimensions T3 and T4, and angle $θ_1$ for polygon 1; dimensions T4 and T5, and angle $θ_2$ for polygon 2; and major and minor axes T6 and T7 for ellipsoid 2. Many other combinations of shapes could be used to characterize the top-view of feature 332 inside unit cell 330. For a detailed description of modeling two-dimensional repeating structures, refer to U.S. patent application Ser. No. 11/061,303, OPTICAL METROLOGY OPTIMIZATION FOR REPETITIVE STRUCTURES, filed on Apr. 27, 2004, which is incorporated herein by reference in its entirety.

Figure 3A:
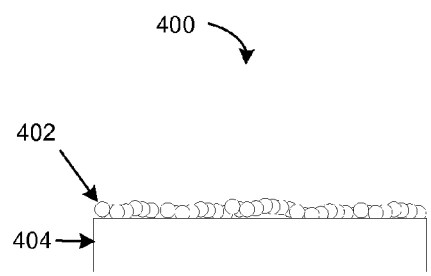
FIG. 3A is an exemplary architectural diagram of two layers of material depicting a substrate and a metal film layer.
Figure 3B:
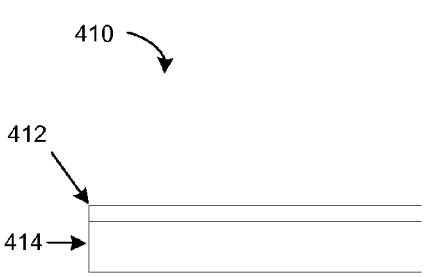
FIG. 3B is an exemplary architectural diagram of two layers of material depicting a substrate and a homogenous metal film layer.

FIG. 3A is an exemplary architectural diagram of a structure 400 comprising a substrate 404 and a metal film layer 402. The metal film layer 402 is inhomogeneous as a result of irregularities of the deposition process. FIG. 3B is an exemplary architectural diagram of structure 410 comprising a substrate 414 and a homogenous metal film layer 412. In general, if the two structures, 400 and 410, depicted in FIGS. 3A and 3B are measured using an optical metrology device such as a reflectometer or ellipsometer (not shown), they will produce different diffraction signals. However, if the sizes of the individual irregularities in the inhomogeneous metal film layer 402 are much smaller than the wavelength of the incident light beam of the optical metrology device, the inhomogeneous metal film layer 402 can be treated as a macroscopically homogenous medium. Optical properties of the inhomogeneous metal film layer 402 can be characterized by an effective dielectric function that is an average of the dielectric functions of air or gas and the metal layer. For a more detailed description of the effective medium theory, refer to Choy, "EFFECTIVE MEDIUM THEORY: PRINCIPLES AND APPLICATIONS", Oxford University Press, 1999, which is incorporated herein by reference in its entirety. The homogenous effective medium characterization of a structure shall hereinafter be referred to as an approximation model and the model that includes the irregularities of the inhomogeneous layer or layers of the structure shall be referred to as the fine model.

Figure 4A:
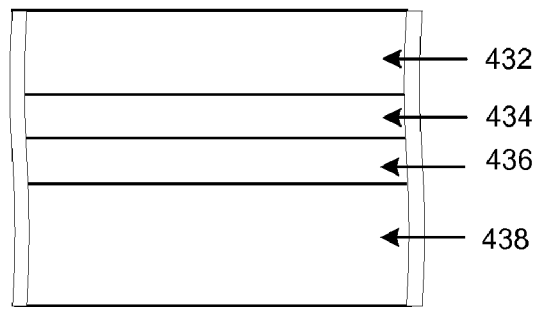
FIG. 4A is an exemplary architectural diagram of an approximation model depicting an unpatterned film stack on a substrate.
Figure 4B:
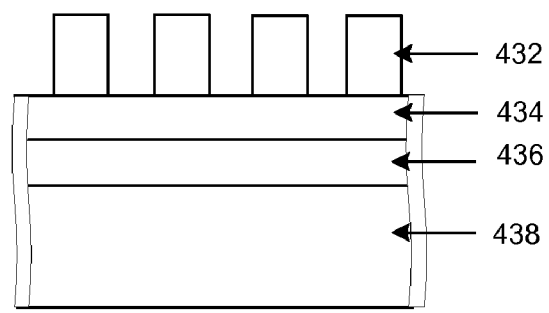
FIG. 4B is an exemplary architectural diagram of a fine model depicting a patterned structure in the top layer of the thin film stack.

FIGS. 4A, 4B, 5A, 5B, and 5C are figures to show two examples of pattern geometries amenable to the application of effective medium theory. FIG. 4A shows an exemplary architectural diagram of an approximation model 430 depicting an unpatterned film stack on a substrate. The approximation model 430 comprises three thin film layers 432, 434, and 436 on top of the substrate 438. FIG. 4B shows an exemplary architectural diagram of a fine model 440 comprising a patterned structure in the top thin film layer 432 of fine model 440. The top thin film layer 432 is patterned into a repeating structure of lines and spaces with no changes to the second and third layer, 434 and 436, and the substrate 438.

Figure 5A:
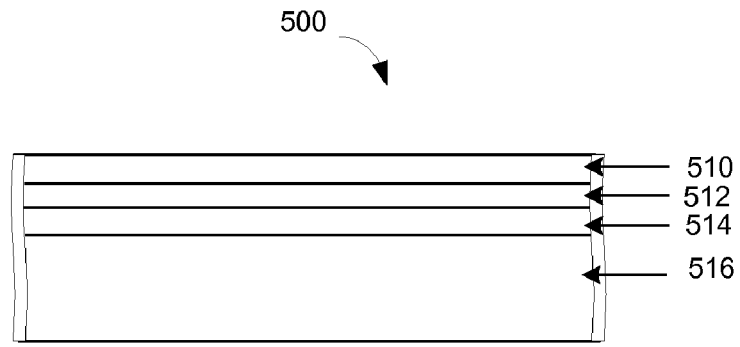
FIG. 5A is an exemplary architectural diagram of an approximation model depicting a stack of thin films on a substrate.
Figure 5B:
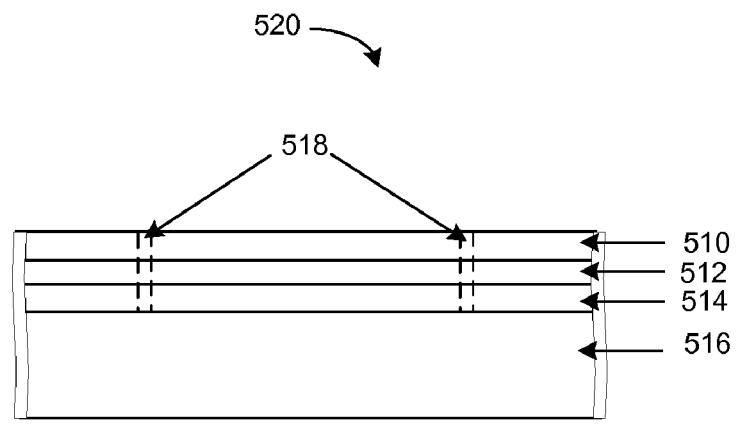
FIG. 5B is an exemplary side-view architectural diagram depicting a stack of thin films with contact holes.
Figure 5C:
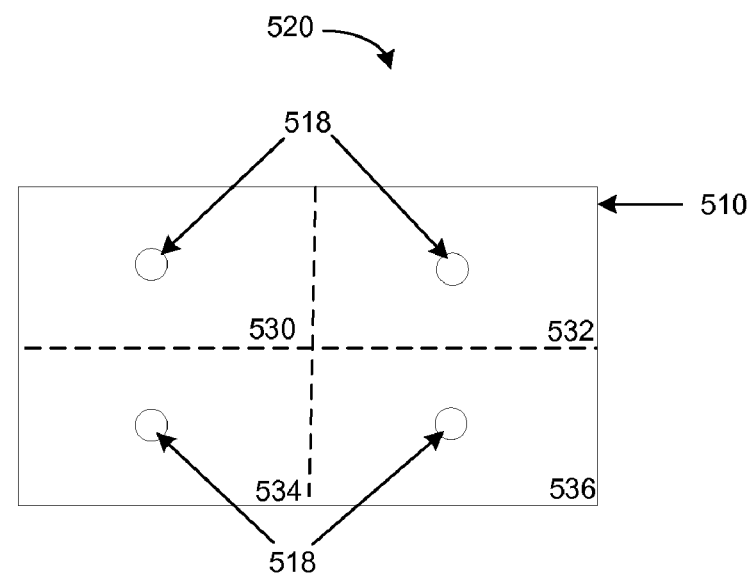
FIG. 5C is an exemplary top-view architectural diagram depicting a stack of thin films with contact holes.

FIG. 5A is an exemplary architectural diagram of an approximation model 500 comprising a stack of thin film layers 510, 512, and 514 on the substrate 516. FIG. 5B is an exemplary side-view architectural diagram of a structure 520 comprising a stack of thin film layers 510, 512, and 514, with contact holes 518 formed in them (shown as dotted lines). FIG. 5C is an exemplary top-view architectural diagram depicting the two-dimensional repeating contact hole structure 520 comprising the top thin film layer 510 and repeating contact holes 518 in the unit cells 530, 532, 534, and 536. The unpatterned stack of thin film layers 510, 512, 514, and the substrate 516, all of structure 500 shown in FIG. 5A, represent the approximation model of structure 520. The repeating contact holes 518 extending through the thin film layers 510, 512, and 514 of FIG. 5B comprise the fine model for the two-dimension repeating contact hole structure. References to a model without qualification mean the same as a profile model. References to an approximation diffraction model include the profile model that is used as an approximation of the structure and the approximation algorithm used to calculate the simulated approximation diffraction signal.

Figure 6A:
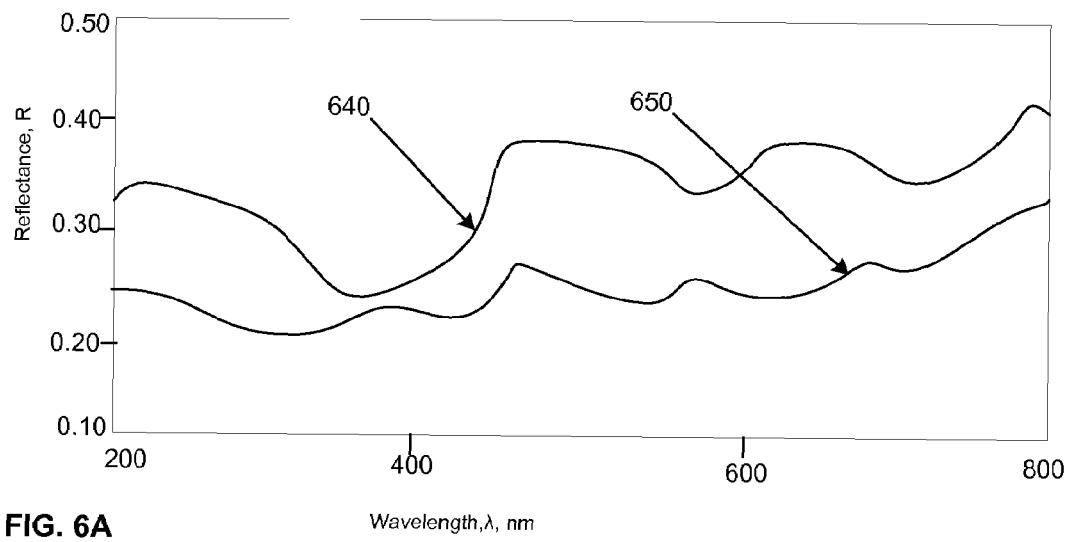
FIG. 6A is an exemplary chart of a simulated fine diffraction signal using a fine diffraction model versus a simulated approximation diffraction signal using an approximation diffraction model of the structure.
Figure 6B:
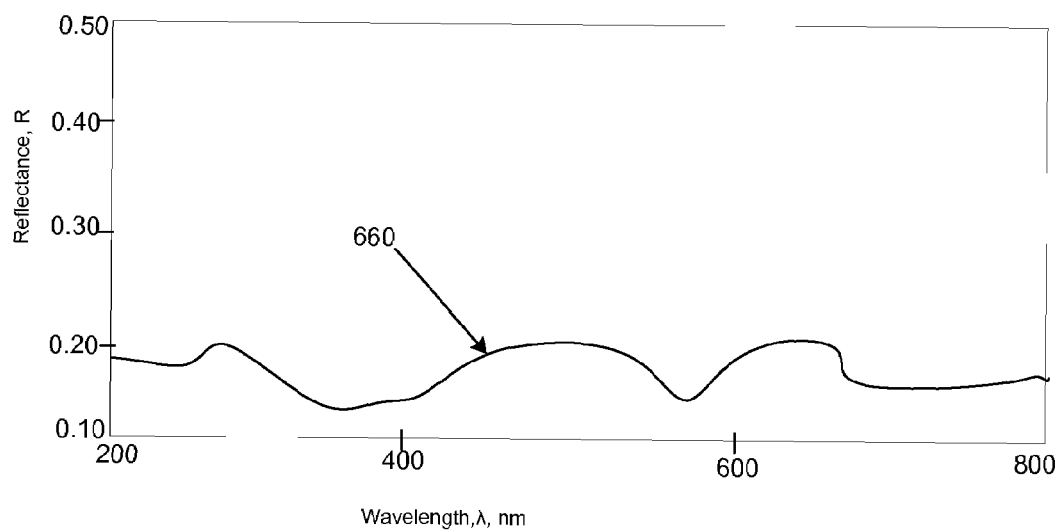
FIG. 6B is an exemplary chart of a calculated difference diffraction signal.

FIG. 6A is an exemplary chart of a simulated fine diffraction signal 640 using a fine model versus a simulated approximation diffraction signal 650 using an approximation model of the structure. As mentioned above, the fine model of the structure may be one-dimensional repeating structure, such as a grating, or lines and spaces or other features, or a repeating two-dimensional structure comprising posts, contact holes, or vias. The simulated fine diffraction signal 640 is generated using a numerical analysis technique such as RCWA, the finite difference method, Green Functions, modal analysis, or the like. For a detailed description of generating a simulated diffraction signal using RCWA, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety. The simulated approximation diffraction signal 650 is based on an approximation model of the structure, such as an unpatterned stack of thin films 430 depicted in FIG. 4A for a grating or the unpatterned stack of thin films 500 depicted in FIG. 5A for a repeating structure comprising contact holes. Referring to FIG. 6A, the difference between the simulated approximation diffraction signal 650 and the simulated diffraction signal 640 is caused by the presence of the structure, which can be lines and spaces in a grating, or the two-dimensional structures such as contact holes or other repeating structures. FIG. 6B is an exemplary chart depicting the difference diffraction signal 660 calculated by subtracting the simulated approximation diffraction signal 650 from the simulated fine diffraction signal 640.

Figure 7A:
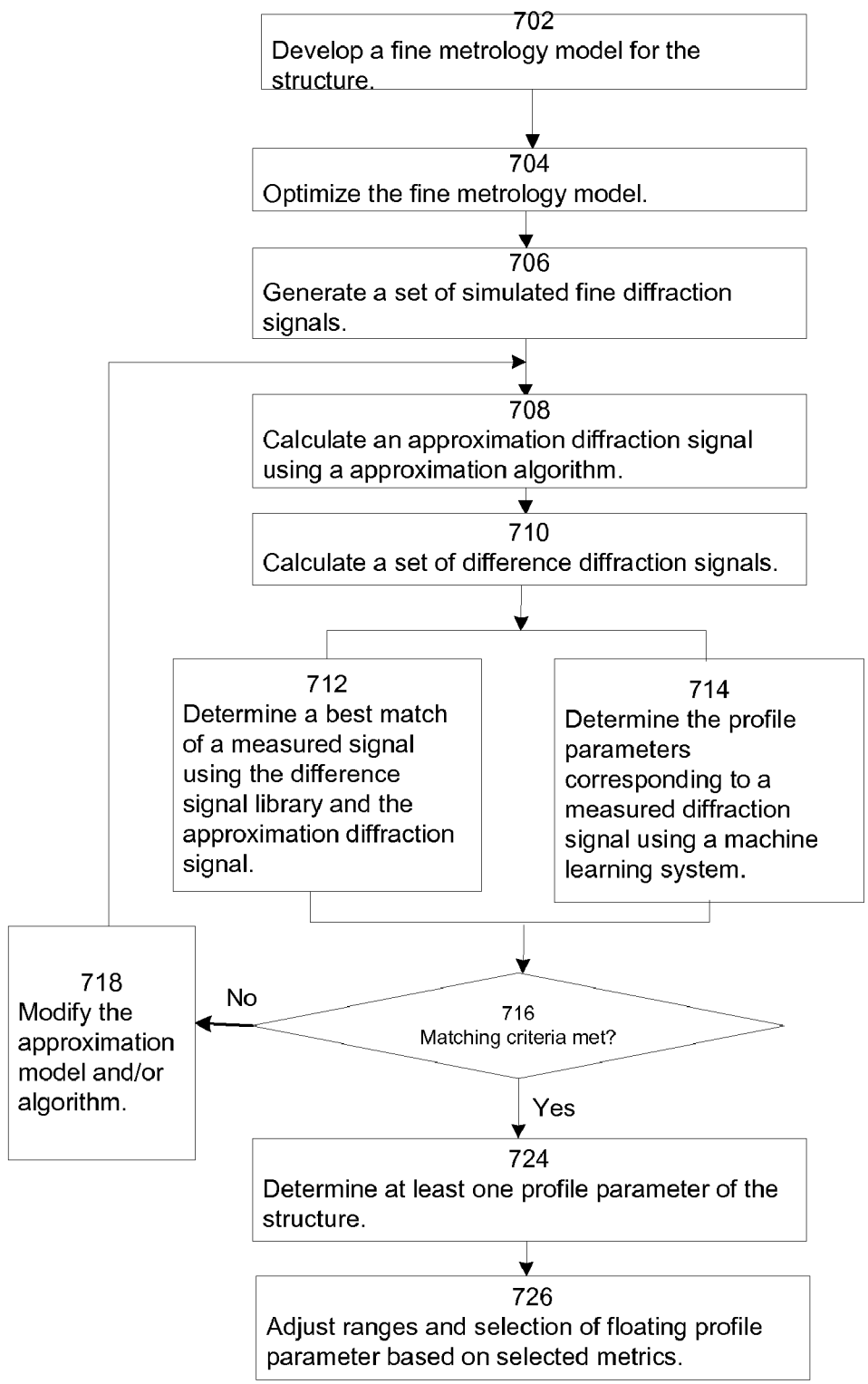
FIG. 7A is an exemplary flowchart for determining profile parameters utilizing approximation and fine diffraction models.

FIG. 7A is an exemplary flowchart for determining profile parameters utilizing approximation and fine diffraction models. In step 702, the metrology model of the structure is developed. The metrology model comprises a profile model of the structure, the diffraction model or models used to calculate simulated diffraction signals, the type and settings of the optical metrology tool used. The profile model typically includes a characterization of the shape and layers of the patterned structure and the number and types of film layers above and/or below the structure. As mentioned above, one calculation of simulated fine diffraction signals involves calculations that utilize the formalism, such as RCWA, related to a solution of Maxwell's electromagnetic equations of diffraction. The optical metrology tool is characterized in the metrology model in terms of whether the tool is a reflectometer, a polarized reflectometer, or an ellipsometer, in the form of technical specifications necessary for simulation of the diffraction signal. The approximation diffraction model characterizes the structure as a macroscopically homogenous effective medium where the optical properties can be described by an effective dielectric function. One example for an approximation diffraction model is to characterize a patterned structure as a series of thin film layers of material. Referring to FIG. 7A, in step 704, the fine metrology model of the structure is optimized, generating an optimized fine profile model. For a detailed description of optical model optimization, refer to U.S. patent application Ser. No. 10/206,491, OPTIMIZED MODEL AND PARAMETER SELECTION FOR OPTICAL METROLOGY, by Vuong, et al., filed on Jun. 27, 2002, which is incorporated in its entirety herein by reference.

In step 706 of FIG. 7A, a set of simulated fine diffraction signals is generated using a set of profile parameters of the optimized fine profile model. The set of profile parameters is generated by using the ranges of the profile parameters and the corresponding resolutions of each profile parameter. For a detailed description of generation of simulated fine diffraction signals using ranges of profile parameters and their corresponding resolutions, refer to U.S. Pat. No. 6,943,900, entitled GENERATION OF A LIBRARY OF PERIODIC GRATING DIFFRACTION SIGNAL, issued on Sep. 13, 2005, which is incorporated herein by reference in its entirety.

Referring to FIG. 7A, in step 708, the simulated approximation diffraction signal is calculated using an approximation algorithm for diffraction simulation. An example of an approximation algorithm for diffraction simulation is the effective medium theory (EMT). Other examples of approximation algorithms for diffraction simulation include coherent potential approximation, random phase approximation, dynamical effective medium theory, or the like. For a more detailed description of other effective medium theory formulations, refer to Choy, "EFFECTIVE MEDIUM THEORY: PRINCIPLES AND APPLICATIONS", Oxford University Press, 1999, and is incorporated in its entirety herein by reference As mentioned above, an approximation diffraction model characterizes the structure as a macroscopically homogenous effective medium where the optical properties can be described by an effective dielectric function. Also mentioned above, one example for an approximation diffraction model is to characterize a patterned structure as a series of thin film layers of material and characterize the optical properties of the thin film layers using the effective dielectric function. In EMT, a periodic or repeating structure may be replaced by an artificial, anisotropic, homogenous medium if only the zeroth diffraction order propagates with evanescent higher diffraction orders and the grating is sufficiently thick that the incident light does not tunnel through. EMT provides a simple second-order expression in a closed form to give an effective index of a grating or repeating structure in the quasi-static limit, of $\Lambda<<\lambda$, with $\Lambda$ and $\lambda$ being the grating period and free-space wavelength of the incident light. In mathematical form:

$$\varepsilon_{\mathit{eff},TE}^2 = \varepsilon_{0,TE} + \frac{\pi^2}{3}f^2(1-f)^2(\varepsilon_A - \varepsilon_B)^2\left(\frac{\Lambda}{\lambda}\right)^2, \qquad 1.1.1$$

$$\varepsilon_{\mathit{eff},TM}^2 = \varepsilon_{0,TM} + \frac{\pi^2}{3}f^2(1-f)^2\left(\frac{1}{\varepsilon_A} - \frac{1}{\varepsilon_B}\right)^2 \varepsilon_{0,TM}^3 \varepsilon_{0,TE}\left(\frac{\Lambda}{\lambda}\right)^2 \qquad 1.1.2$$

where $f$ is the grating volume fill factor, and $\varepsilon_A$ and $\varepsilon_B$ are relative permittivities of the grating materials. The zeroth-order permittivity $\varepsilon_0$ in equation 1.1.1 and 1.1.2 is given by:

$$\varepsilon_{0,TE} = f\varepsilon_A + (1-f)\varepsilon_B \qquad 1.1.3$$

$$\varepsilon_{0,TM} = \frac{\varepsilon_A \varepsilon_B}{f\varepsilon_B + (1-f)\varepsilon_A}. \qquad 1.1.4$$

For a more detailed description of the calculation of simulated approximation diffraction signal using EMT and variations of EMT, refer to Moon, et al., "FITTING-BASED DETERMINATION OF AN EFFECTIVE MEDIUM OF A METALLIC PERIODIC STRUCTURE AND APPLICATION TO PHOTONIC CRYSTALS", Vol. 23, No. 1, January 2006, J. Opt. Soc. of America, which is incorporated in its entirety herein by reference. It is understood that many variations and adaptations of the basic equations above are applicable and may be used in the methods and systems described herewith.

In step 710, the difference diffraction signal is calculated by subtracting the simulated approximation diffraction signal from the simulated fine diffraction signal. In step 712, a best match to a measured diffraction signal scattered off of the structure is determined using a library of difference diffraction signals and the calculated approximation diffraction signal The library of difference diffraction signals may be created from the set of simulated difference diffraction signals and their corresponding profile model parameters selected in steps 702-710. The calculated approximation diffraction signal is subtracted from the measured diffraction signal and the resulting adjusted measured diffraction signal is matched against the library to get a best match. Alternatively, in step 714, the profile parameters corresponding to a measured diffraction signal may be determined using a machine learning systems (MLS) trained with the sets of simulated difference diffraction signals and their corresponding profile parameters. The MLS is trained to process a difference diffraction signal as input and generate profile parameters as output. The calculated approximation diffraction signal is subtracted from the measured diffraction signal, resulting in an adjusted measured diffraction signal, which is input to the trained MLS, generating profile parameters as output. For a more detailed description of machine learning systems, see U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

Referring to FIG. 7A, in step 716, one or more matching criteria are compared with calculated matching criteria using the results of step 712 or 714. The one or more matching criteria may include a goodness of fit (GOF) of the difference diffraction signal from the library, or generated by the MLS versus the adjusted measured diffraction signal. Alternatively, a cost function target between the difference diffraction signal from the library, or generated by the MLS, versus the adjusted measured diffraction signal, may be used. If the one or more matching criteria are not met, in step 718, the approximation model and/or the approximation algorithm are modified. Modification of the approximation model may involve, for example, floating the thickness of one or more of the layers, or conversely, changing a previously floating thickness to a fixed value. Modification of the approximation algorithm to calculate the approximation diffraction signal comprises the use of a variant of the effective medium theory formula, or switching from effective medium theory to another approximation theory, such as coherent potential approximation, random phase approximation, dynamical effective medium theory, or the like. Steps 708, 710, 712 or 714, and 716 are iterated until the one or more matching criteria are met.

Still referring to FIG. 7A, if the one or more matching criteria are met, in step 724, at least one determined profile parameter of the structure is utilized in subsequent device processing. Profile parameters of the optimized profile model typically include low and high ranges of thicknesses; for example, a top CD range may have a low value of 25 nm and a high value of 40 nm. In step 726, the ranges of profile parameters of the optimized profile are adjusted by limiting or expanding the range as a result of sensitivity analysis or other statistical analysis of the effects of the just-determined profile parameter on the measured diffraction signal. In some cases, a profile parameter may not alter the measured diffraction signal, i.e., the measured diffraction signal is insensitive to changes of the particular profile parameter. In this case, the particular profile parameter may be set to a fixed value for subsequent library and MLS processing. Conversely, if the just-determined parameter does alter the measured diffraction signal significantly, then widening the range of variation, or increasing its resolution may be required. In an alternate embodiment, thicknesses and/or widths of thin film layers may be fixed or floated, or the refractive indices and/or the extinction coefficients of layers may fixed or floated, based on the sensitivity analysis, or other metrics analyzed. For a more detailed description of sensitivity analysis and use of goals or metrics, see U.S. patent application Ser. No. 10/946,729, titled OPTICAL METROLOGY MODEL OPTIMIZATION BASED ON GOALS, filed on Sep. 21, 2004, which is incorporated herein by reference in its entirety.

Figure 7B:
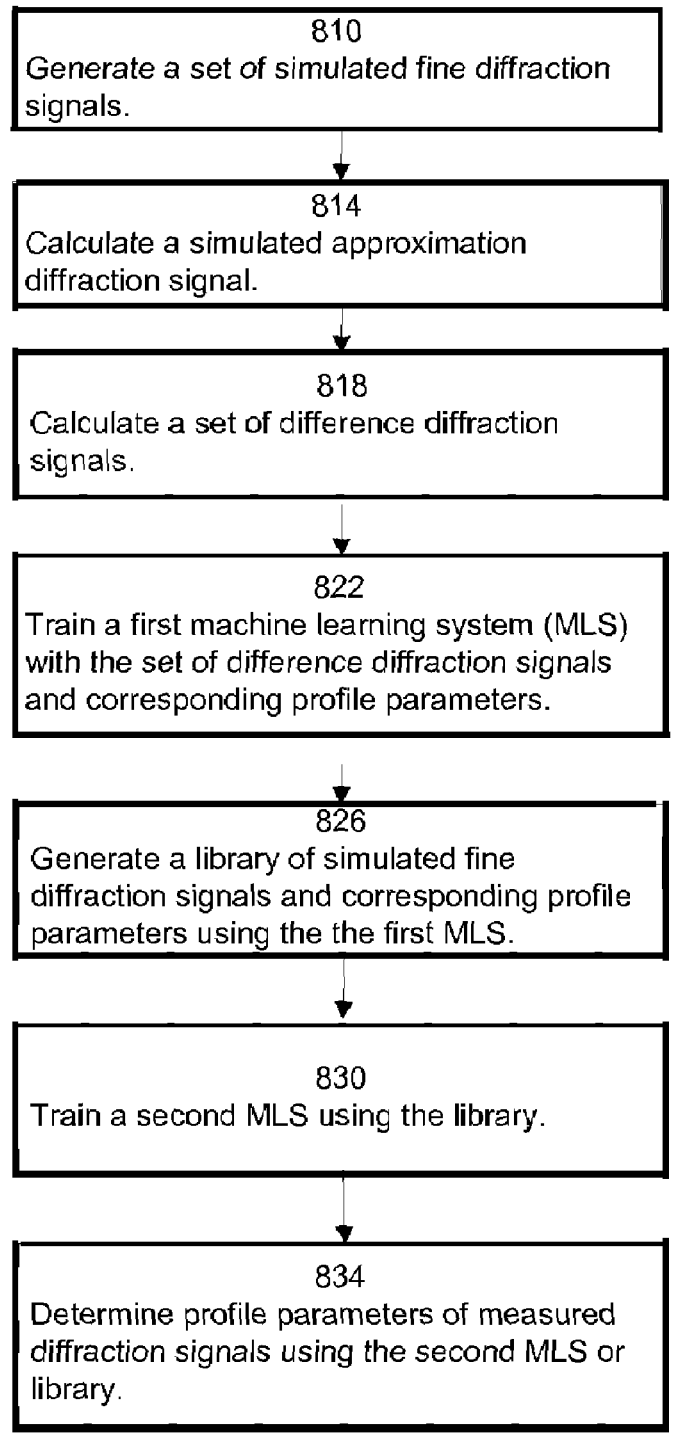
FIG. 7B is an exemplary flowchart for determining profile parameters utilizing approximation and fine diffraction models using a first and a second machine learning systems.

FIG. 7B shows an exemplary flowchart for determining profile parameters utilizing approximation and fine diffraction models using a first and a second machine learning system. In step 810, a set of simulated fine diffraction signals is generated using an optimized fine profile model. In step 814, a simulated approximation diffraction signal is calculated, where the calculation performed is similar to that of step 708 of FIG. 7A. Referring to FIG. 7B, in step 818, a set of difference diffraction signals is calculated by subtracting the simulated approximation diffraction signal from each simulated fine diffraction signal. In step 822, a first MLS is trained with the set of difference diffraction signals and corresponding profile parameters, the first machine learning system being trained to process profile parameters as input and generate a difference diffraction signal as output. In step 826, using the ranges of the profile parameters of the optimized profile model and the resolution of each profile parameter, the first MLS is used to generate difference diffraction signals corresponding to various combinations of profile parameters. The simulated approximation diffraction signal calculated in step 814 is added to the difference diffraction signal and stored in a library of simulated fine diffraction signals, along with the profile parameters corresponding to the simulated fine diffraction signals. In step 830, a second MLS is trained using the generated library where the second MLS is trained to process simulated or measured fine diffraction signals as input and generate profile parameters as output. In step 834, the second MLS or the generated library are used to determine profile parameters from measured diffractions signals.

In an alternative embodiment, the second MLS is trained in a different manner than described above, i.e., the second MLS is trained to process profile parameters as input and generate fine diffraction signals as output. Trial profile parameters are input to the second MLS to generate a fine diffraction signal that is compared to the measured diffraction signal. If one or more matching criteria such as GOF and/or cost function are not met in the comparison, then another set of trial profile parameters is used and the process is iterated using regression techniques to converge to the set of trial profile parameters that meet the one or more matching criteria.

Figure 7C:
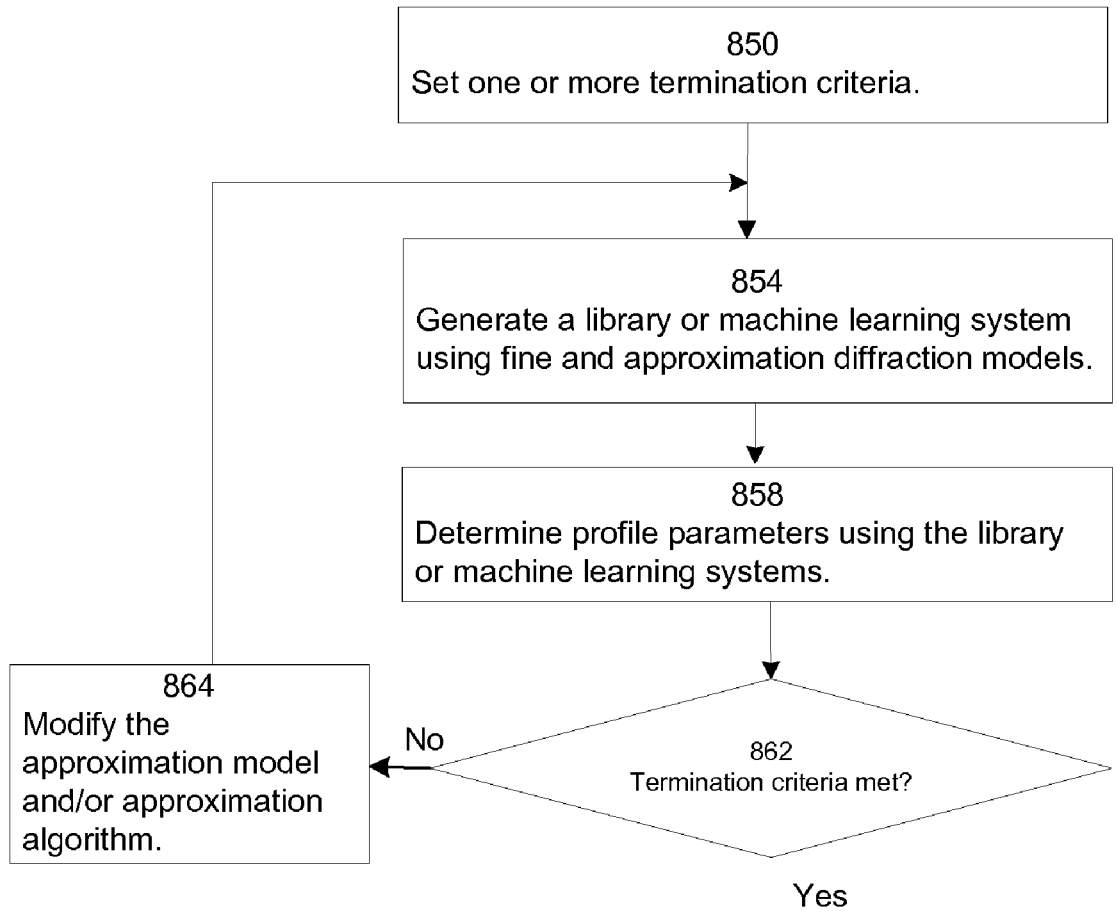
FIG. 7C is an exemplary flowchart for determining profile parameters utilizing approximation and fine diffraction models using one or more termination criteria for metrology model optimization.

FIG. 7C is an exemplary flowchart for determining profile parameters utilizing approximation and fine diffraction models using one or more termination criteria for metrology model optimization. Referring to FIG. 7C, in step 850, one or more termination criteria for the diffraction model optimization process may be set. An example of a termination criterion may be repeatability of the measurements using the optimized diffraction model. Other termination criteria include accuracy of measurements compared to the measurements with a reference tool such as a scanning electron microscope (SEM), ranges of precision, critical dimension uniformity, correlation coefficient, goodness-of-fit, cost function, throughput, closeness of match of measurements made with different metrology devices, and the like. Closeness of match of measurements made with different metrology devices may include one or more of the absolute measurement difference, average correlation ratio between a metrology system and a reference metrology system, the standard mean deviation (σ) and its multiples, and the total measurement uncertainty. In step 854, a library of difference diffraction signals and corresponding profile parameters is generated or an MLS is trained on pairs of difference diffraction signals and corresponding profile parameters, where the difference diffraction signals are generated using fine and approximation diffraction models. Generation of the library and the trained MLS are similar to the methods described in the flowcharts depicted in FIGS. 7A and 7B.

Referring to FIG. 7C, in step 858, the library or trained MLS is used to determine profile parameters of the structure using measured diffraction signals. Use of the library and the trained MLS for determining profile parameters are also described in the description of the flowcharts depicted in FIGS. 7A and 7B. In step 862, if the calculated one or more termination criteria does not meet the set one or more termination criteria, then in step 864 the approximation model is modified and/or the approximation algorithm is modified. For example, if the set termination criterion is accuracy of the measurement compared to measurement of the structure using a SEM, and assuming that the approximation model used is a structure of fixed thickness and width thin film layers, this model may then be modified by, for example, floating the thickness of one or more of the film layers. Alternatively, if the approximation algorithm used the effective medium theory equations, the approximation algorithm may be modified to use a variation of the medium theory equations or switch to coherent potential approximation, random phase approximation, or dynamical effective medium theory. It is understood that other approximation models may be used, such as variations of EMT where of the layer properties are fixed or floated, or where the refractive indices and/or the extinction coefficients of a layers are fixed or floated. The variations of the approximation model can be matched with other approximation algorithms mentioned above, or the like.

Figure 8:
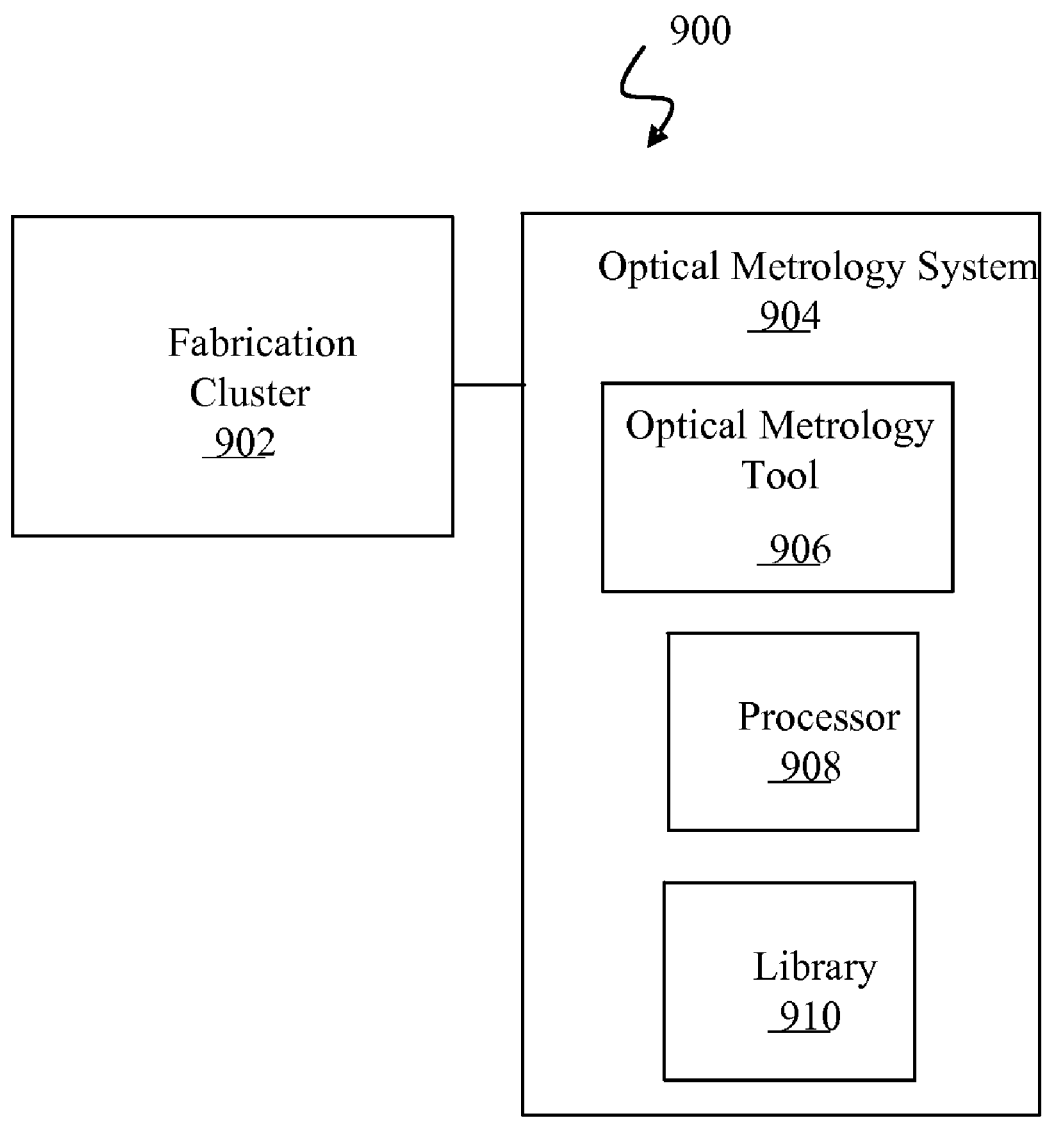
FIG. 8 is an exemplary block diagram of a system for utilizing a library developed for determining the profile parameters of a structure using approximation and fine diffraction models.

FIG. 8 is an exemplary block diagram of a system for utilizing a library developed for determining the profile parameters of a structure using approximation and fine diffraction models. In one exemplary embodiment, optical metrology system 904 can also include a library 910 with a plurality of simulated difference diffraction signals and a plurality of profile parameters associated with the plurality of simulated difference diffraction signals. As described above, the library 910 can be generated in advance. Metrology processor 908 can calculate a simulated approximation diffraction signal and can compare a measured diffraction signal off of a structure fabricated in fabrication cluster 902, adjusted by subtracting the simulated approximation diffraction signal, to the plurality of simulated difference diffraction signals in the library When a matching simulated difference diffraction signal is found, the profile parameters associated with the matching simulated difference diffraction signal in the library are assumed to correspond to the profile parameters of the actual structure measured by the metrology tool 906.

Figure 9:
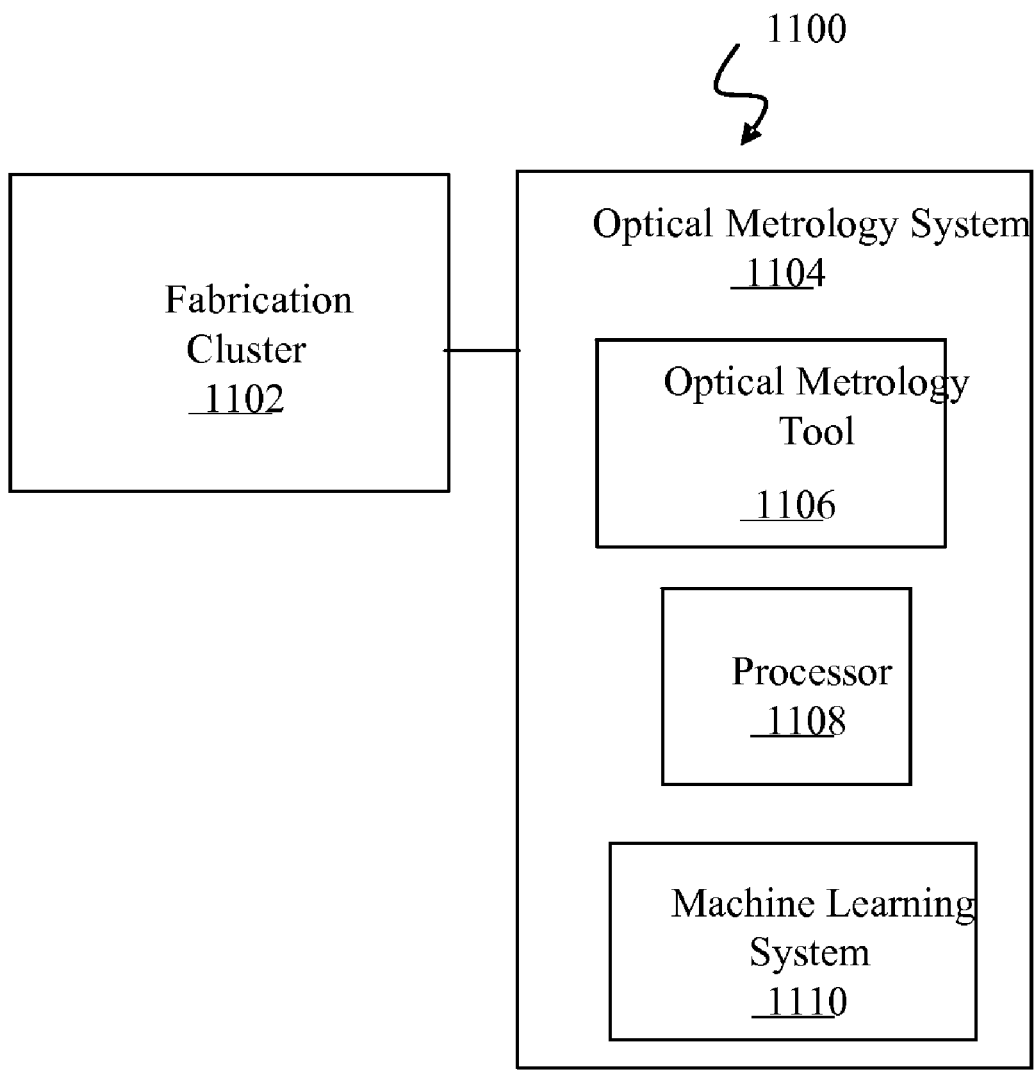
FIG. 9 is an exemplary block diagram of a system for utilizing a machine learning system developed for determining the profile parameters of a structure using approximation and fine diffraction models.

FIG. 9 is an exemplary block diagram of a system for utilizing a machine learning system developed for determining the profile parameters of a structure using approximation and fine diffraction models. System 1100 includes a fabrication cluster 1102 and an optical metrology system 1104. Fabrication cluster 1102 is configured to perform wafer processing to fabricate a structure on a wafer. Optical metrology system 1104 includes an optical metrology tool 1106, a processor 1108, and a machine learning system 1110. Optical metrology tool 1106 can comprise components of a scatterometry device, such as a reflectometer, ellipsometer, and the like. The optical metrology tool 1106 is configured to measure a set of diffraction signals off of the structure. Processor 1108 is configured to calculate a simulated approximation diffraction signal, and is also configured to train machine learning system 1110 using the set of measured diffraction signals as inputs, and profile parameters as the expected outputs of machine learning system 1110.

After machine learning system 1110 has been trained, optical metrology system 1100 can be used to determine one or more values of one or more profile parameters of a structure on the wafer. In particular, a structure is fabricated using fabrication cluster 1102 or another fabrication cluster. A diffraction signal is measured off of the structure using optical metrology tool 1106. The measured diffraction signal, adjusted by subtracting the simulated approximation diffraction signal, is input into the trained machine learning system 1110 to obtain one or more values of profile parameters as an output. In one exemplary embodiment, machine learning system 1110 comprises two machine learning systems trained and utilized as specified in the method described in connection with FIG. 7C.

Figure 10:
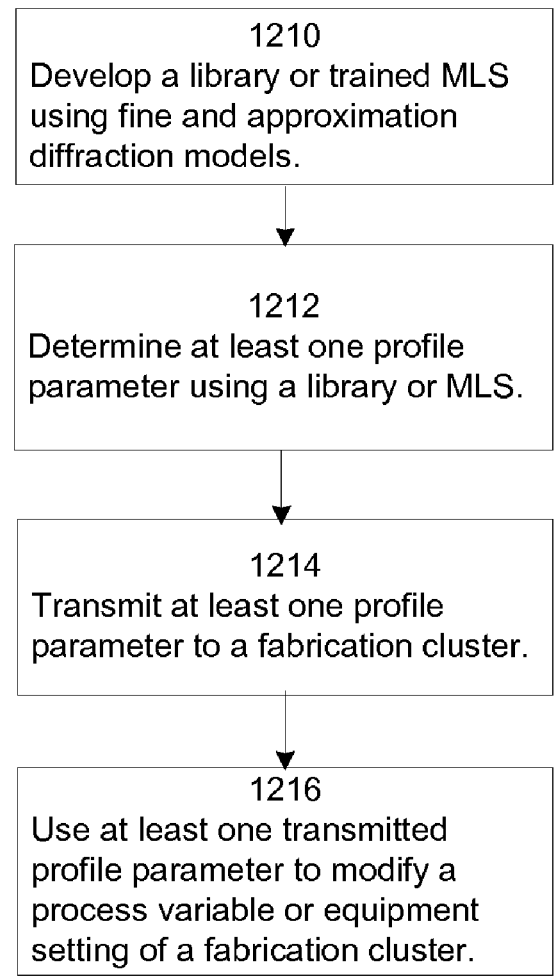
FIG. 10 is an exemplary flowchart for determining and utilizing profile parameters using approximation and fine diffraction models for automated process and equipment control.

FIG. 10 is an exemplary flowchart for determining and utilizing profile parameters using approximation and fine diffraction models for automated process and equipment control. In step 1210, a library and/or trained MLS using fine and approximation diffraction models are developed, as described above. In step 1212, at least one profile parameter of a structure is determined using the library or the trained MLS. In step 1214, the at least one profile parameter is transmitted to a fabrication cluster configured to perform a processing step, where the processing step may be executed in the semiconductor manufacturing process flow either before or after measurement step 1212 is made. In step 1216, the at least one transmitted profile parameter is used to modify a process variable or equipment setting for the processing step performed by the fabrication cluster.

Figure 11:
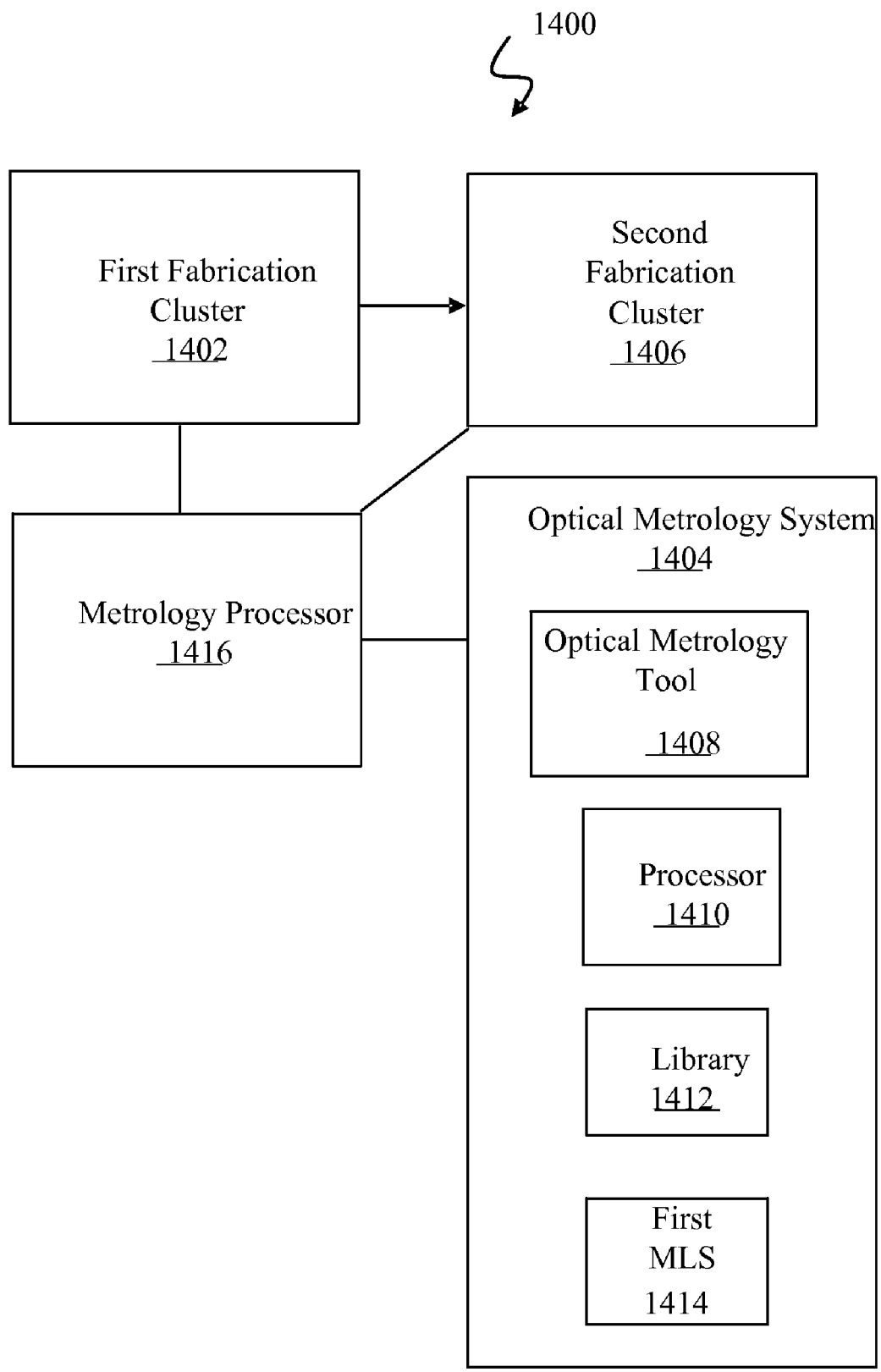
FIG. 11 is an exemplary block diagram for determining and utilizing profile parameters for automated process and equipment control.

FIG. 11 is an exemplary block diagram of a system for determining and utilizing profile parameters for automated process and equipment control. System 1400 includes a first fabrication cluster 1402 and optical metrology system 1404. System 1400 also includes a second fabrication cluster 1406. Although the second fabrication cluster 1406 is depicted in FIG. 11 as being subsequent to first fabrication cluster 1402, it should be recognized that second fabrication cluster 1406 can be located prior to first fabrication cluster 1402 in system 1400 (e.g. and in the manufacturing process flow).

A photolithographic process, such as exposing and/or developing a photoresist layer applied to a wafer, can be performed using first fabrication cluster 1402. Optical metrology system 1404 is similar to optical metrology system 40 of FIG. 1A. In one exemplary embodiment, optical metrology system 1404 includes an optical metrology tool 1408 and processor 1410. Optical metrology tool 1408 is configured to measure a diffraction signal off of the structure. Processor 1410 is configured to compare the measured diffraction signal, adjusted by subtracting the simulated approximation diffraction signal, to a difference diffraction signal. The difference diffraction signal was generated using approximation and fine diffraction models as described above. If the measured diffraction signal, adjusted by the simulated approximation diffraction signal, and the stored difference diffraction signal match, one or more values of the profile parameters are determined to be the one or more values of the profile parameters associated with the stored difference diffraction signal.

In one exemplary embodiment, optical metrology system 1404 can also include a library 1412 with a plurality of simulated fine diffraction signals and a plurality of values of one or more profile parameters associated with the plurality of simulated fine diffraction signals. As described above, the library can be generated in advance; metrology processor 1410 can compare a measured diffraction signal off a structure to the plurality of simulated fine diffraction signals in the library. When a matching simulated fine diffraction signal is found, the one or more values of the profile parameters associated with the matching simulated fine diffraction signal in the library is assumed to be the one or more values of the profile parameters used in the wafer application to fabricate the structure.

System 1400 also includes a metrology processor 1416. In one exemplary embodiment, processor 1410 can transmit the one or more values of the one or more profile parameters to metrology processor 1416. Metrology processor 1416 can then adjust one or more process parameters or equipment settings of first fabrication cluster 1402 based on the one or more values of the one or more profile parameters determined using optical metrology system 1404. Metrology processor 1416 can also adjust one or more process parameters or equipment settings of the second fabrication cluster 1406 based on the one or more values of the one or more profile parameters determined using optical metrology system 1404. As noted above, fabrication cluster 1406 can process the wafer before or after fabrication cluster 1402. In another exemplary embodiment, processor 1410 is configured to train machine learning system 1414 using the set of measured diffraction signals as inputs to machine learning system 1414 and profile parameters as the expected outputs of machine learning system 1414. In one exemplary embodiment, machine learning system 1414 comprises two machine learning systems trained and utilized as specified in the method described in connection with FIG. 7C.

Furthermore, a computer readable medium (not shown) such as computer memory, disk, and/or storage may be used to store the instructions and computer programs to determine one or more profile parameters of a structure using an optical metrology model, the optical metrology model comprising a profile model, an approximation diffraction model, and a fine diffraction model, the difference diffraction signal and corresponding profile parameters stored in a library. Another embodiment, similar computer-executable instructions may be stored in a computer readable medium such as computer memory, disk, and/or storage to determine one or more profile parameters of a structure using a similar optical metrology model and using the difference diffraction signal and corresponding profile parameters in training an MLS. In yet another embodiment, similar computer-executable instructions may be stored in a computer readable medium such as computer memory, disk, and/or storage to control a photolithography cluster or other fabrication cluster using determined one or more profile parameters using the aforementioned methods to control a fabrication cluster.

Although exemplary embodiments have been described, various modifications can be made without departing from the spirit and/or scope of the present invention. Therefore, the present invention should not be construed as being limited to the specific forms shown in the drawings and described above.

We claim:

1. A method of controlling a fabrication cluster using a library developed using an optical metrology model, the optical metrology model comprising a profile model, an approximation diffraction model, and a fine diffraction model, the method comprising:
   (a) developing a metrology model of a structure, the metrology model including a profile model, the profile model having profile parameters;
   (b) optimizing the metrology model, the optimized metrology model including an optimized profile model, (c) calculating a simulated approximation diffraction signal based on the approximation diffraction model of the structure;
(d) generating a set of simulated fine diffraction signals from a set of profile parameters, the simulated fine diffraction signals generated using the optimized profile model of the structure;
(e) generating a library of difference diffraction signals and corresponding profile parameters, the difference diffraction signal calculated by subtracting the simulated approximation diffraction signal from each of the simulated fine diffraction signal of the set of simulated fine diffraction signals;
(f) determining a best match of a measured diffraction signal adjusted by the simulated approximation diffraction signal against the library of difference diffraction signals;
(g) if one or more matching criteria are met, determining at least one profile parameter of the structure,
else modifying the approximation diffraction model and iterating steps (c) through (g) until the one or more matching criteria are met;
(h) transmitting the at least one profile parameter to a fabrication cluster wherein the fabrication cluster was used to create the structure, the fabrication cluster having process parameters and equipment settings; and
(i) adjusting one or more process parameters or equipment settings of the fabrication cluster based on the at least one profile parameter.

2. The method of claim 1 wherein the structure is a grating or a repeating structure.

3. The method of claim 1 wherein calculating the simulated approximation diffraction signal utilizes an approximation algorithm for the diffraction simulation.

4. The method of claim 3 wherein the approximation algorithm for diffraction simulation uses effective medium theory.

5. The method of claim 4 wherein the effective medium theory replaces a periodic structure or a repeating structure with an anisotropic homogenous medium with an effective permittivity.

6. The method of claim 3 wherein the approximation algorithm for diffraction simulation uses coherent potential approximation, random phase approximation or dynamical effective medium theory.

7. The method of claim 1 wherein the fabrication cluster is a photolithography, etch, physical vapor deposition, chemical vapor deposition, or chemical-mechanical polishing cluster.

8. A method of controlling a fabrication cluster using a machine learning system, the machine learning system trained developed using an optical metrology model, the optical metrology model comprising a profile model, an approximation diffraction model, and a fine diffraction model, the method comprising:
(a) developing a metrology model of a structure, the metrology model including a profile model, the profile model having profile parameters;
(b) optimizing the metrology model, the optimized metrology model including an optimized profile model,
(c) calculating a simulated approximation diffraction signal based on the approximation diffraction model of the structure;
(d) generating a set of simulated fine diffraction signals from a set of profile parameters, the simulated fine diffraction signals generated using the optimized profile model of the structure;
(e) calculating a set of difference diffraction signal by subtracting the simulated approximation diffraction signal from each of the simulated fine diffraction signals of the set of simulated fine diffraction signals and pairing each difference diffraction signal with the corresponding profile parameters;
(f) training a machine learning system using the pairs of difference diffraction signal and corresponding profile parameters, the machine learning system trained to process the difference diffraction signal as input and generate the profile parameters as output;
(g) subtracting the simulated approximation diffraction signal from a measured diffraction signal resulting in an adjusted measured diffraction signal;
(h) using the trained machine learning system, inputting the adjusted measured diffraction signal and generating profile parameters;
(i) if one or more matching criteria are met, accessing at least one generated profile parameter;
(j) transmitting at least one profile parameter of the generated corresponding profile parameters to a fabrication cluster wherein the fabrication cluster was used to create the structure, the fabrication cluster having process parameters and equipment settings; and
(k) adjusting one or more process parameters or equipment settings of the fabrication cluster based on the at least one profile parameter.

9. The method of claim 8 wherein the structure is a grating or a repeating structure.

10. The method of claim 8 wherein calculating the simulated approximation diffraction signal includes utilizing an approximation algorithm for diffraction simulation.

11. The method of claim 10 wherein the approximation algorithm for diffraction simulation uses effective medium theory.

12. The method of claim 10 wherein the approximation algorithm for diffraction simulation uses coherent potential approximation, random phase approximation or dynamical effective medium theory.

13. A method of controlling a fabrication cluster using a machine learning system and an optical metrology model, the optical metrology model comprising a profile model, an approximation diffraction model, and a fine diffraction model, the method comprising:
generating a set of simulated fine diffraction signals from a set of profile parameters using a fine diffraction model;
calculating a simulated approximation diffraction signal based on the approximation diffraction model of the structure;
calculating a set of difference diffraction signals by subtracting the simulated approximation diffraction signal from each fine diffraction signal of the set of simulated fine diffraction signals;
training a first machine learning system with the set of difference diffraction signals and corresponding profile parameters, the first machine learning system trained to process profile parameters as input and generate a difference diffraction signal as output;
generating a library of simulated fine diffraction signals and profile parameters using the trained first machine learning system and using ranges and corresponding resolutions of the profile parameters;
training a second machine learning systems using the generated library, the second machine learning systems trained to process measured diffraction signals as input and generate profile parameters as output;
determining at least one profile parameter from a measured diffraction signal using the generated library or the trained second machine learning system;

transmitting the at least one profile parameter to a fabrication cluster wherein the fabrication cluster was used to create the structure, the fabrication cluster having process parameters and equipment settings; and adjusting one or more process parameters or equipment settings of the fabrication cluster based on the at least one profile parameter.

14. The method of claim 13 wherein the structure is a grating or a repeating structure.

15. The method of claim 13 wherein calculating the simulated approximation diffraction signal utilizes an approximation algorithm for diffraction simulation.

16. The method of claim 15 wherein the approximation algorithm for diffraction simulation uses the effective medium theory, coherent potential approximation, random phase approximation or dynamical effective medium theory.

17. A system for controlling a fabrication cluster using a machine learning system developed using an optical metrology model, the optical metrology model comprising a profile model, an approximation diffraction model, and a fine diffraction model of a structure having a profile, the profile having profile parameters, the system comprising:

an optical metrology tool configured to illuminate the structure with an illumination beam and detect the diffraction signal off the structure;

a processor configured to generate a simulated approximation diffraction signal off the structure based on an approximation diffraction model of the structure and approximation algorithm for diffraction simulation, generate a simulated fine diffraction signal off the structure based on a fine diffraction model of the structure and the profile parameters, and calculate a difference diffraction signal by subtracting the approximation diffraction signal from the simulated fine diffraction signal;

a machine learning system trained with pairs of difference diffraction signal and corresponding profile parameters and configured to process a difference diffraction signal as input and generate profile parameters as output; and a fabrication cluster configured to perform a process on the structure, the process controlled by process variables and equipment settings;

wherein the structure is measured by the optical metrology tool generating a measured diffraction signal, the simulated approximation diffraction signal is subtracted from the measured diffraction signal generating an adjusted measured diffraction signal, the adjusted measured diffraction signal is input into the trained machine learning system, the trained machine learning system generates profile parameters as output, and at least one generated profile parameter is used to modify a process variable or equipment setting of the fabrication cluster.

18. A system for controlling a fabrication cluster using a machine learning system developed using an optical metrology model, the optical metrology model comprising a profile model, an approximation diffraction model, and a fine diffraction model of a structure having a profile, the profile having profile parameters, the system comprising:

an optical metrology tool configured to illuminate the structure with an illumination beam and detect the diffraction signal off the structure;

a processor configured to generate a simulated approximation diffraction signal off the structure based on an approximation diffraction model of the structure and approximation algorithm for diffraction simulation, generate a simulated fine diffraction signal off the structure based on a fine diffraction model of the structure and the profile parameters, and calculate a difference diffraction signal by subtracting the approximation diffraction signal from the simulated fine diffraction signal;

a first machine learning system trained with pairs of difference diffraction signal and corresponding profile parameters and configured to process profile parameters as input and generate difference diffraction signal as output;

a fabrication cluster configured to perform a process on the structure, the process controlled by process variables and equipment settings; and a second machine learning system trained with pairs of profile parameters and associated simulated diffraction signals and configured to process measured diffraction signals as input and generate profile parameters as output;

wherein the processor creates a set of pairs of difference diffraction signals and corresponding profile parameters, trains the first machine learning system with the set of pairs of difference diffraction signals and corresponding profile parameters to process profile parameters as input and generate difference diffraction signal as output, generates a library of simulated fine diffraction signals and profile parameters, trains the second machine learning systems using the library to process measured diffraction signals as input and generate profile parameters as output; and wherein the structure is measured by the optical metrology tool generating a measured diffraction signal, the measured diffraction signal is input into the second machine learning system, and the second machine learning system generates at least one profile parameter as output, the at least one profile parameter is transmitted to the fabrication cluster, and the at least one profile parameter is used to modify at least one process variable or at least one equipment setting of the fabrication cluster.

19. The system of claim 18 wherein the fabrication cluster is a photolithography, etch, physical vapor deposition, chemical vapor deposition, or chemical-mechanical polishing cluster.

20. The system of claim 18 wherein the fabrication cluster is a photolithography, etch, physical vapor deposition, chemical vapor deposition, or chemical-mechanical polishing cluster.

* * * * *